United States Patent [19]

Mehta et al.

[11] Patent Number: 6,001,800

[45] Date of Patent: Dec. 14, 1999

[54] SPRAY DRIED ERYTHROPOIETIN

[75] Inventors: Deepak B. Mehta, Warren; Diane C. Corbo, Flemington, both of N.J.; Kurshid Iqbal, Berwyn, Pa.

[73] Assignee: Ortho Pharmaceutical Corp., Raritan, N.J.

[21] Appl. No.: 08/894,023

[22] PCT Filed: Dec. 15, 1996

[86] PCT No.: PCT/US95/16416

§ 371 Date: May 15, 1998

§ 102(e) Date: May 15, 1998

[87] PCT Pub. No.: WO96/18647

PCT Pub. Date: Jun. 20, 1996

Related U.S. Application Data

[63] Continuation-in-part of application No. 08/357,947, Dec. 16, 1994, abandoned.

[51] Int. Cl.$^6$ .......................... A61K 38/16; A61K 38/17; C07K 1/14; C07K 14/505
[52] U.S. Cl. .................................. 514/8; 514/2; 530/380; 530/399; 530/412; 530/427
[58] Field of Search ..................................... 530/412, 350, 530/380, 399, 418, 419, 420, 421, 422, 427; 514/2, 8, 12, 21

[56] References Cited

U.S. PATENT DOCUMENTS

| | | | |
|---|---|---|---|
| 4,397,840 | 8/1983 | Takezawa et al. | 514/8 |
| 4,806,524 | 2/1989 | Kawaguchi et al. | 514/8 |
| 4,992,419 | 2/1991 | Woog | 514/8 |
| 5,354,934 | 10/1994 | Pitt et al. | 514/8 |

FOREIGN PATENT DOCUMENTS

91/11200  of 1991  WIPO .

OTHER PUBLICATIONS

Broadhead et al. Drug Dev. Ind. Pharm. 18(11–12): 1169–1206.

*Primary Examiner*—Nancy Degen
*Attorney, Agent, or Firm*—John W. Wallen, III

[57] ABSTRACT

A method of preparing spray dried recombinant erythropoietin (rhEPO) is disclosed. The method comprises providing an aqueous solution of rhEPO and atomizing the solution into a spray drying the spray and separating the dried rhEPO from the drying air. Also disclosed is rhEPO made by the disclosed method.

9 Claims, No Drawings

SPRAY DRIED ERYTHROPOIETIN

This is a 371 of PCT/US95/16416 filed Dec. 15, 1996, which is continuation-in-part of application Ser. No. 08/357,947, filed Dec. 16, 1994, now abandoned.

This invention concerns a method for the preparation of spray dried erythropoietin and the dry erythropoietin powder produced thereby.

BACKGROUND OF THE INVENTION

Erythropoietin (EPO) is a glycoprotein hormone primarily synthesized in the kidney and is the chief regulator of red blood cell production in the body. Commercially available human EPO is produced via recombinant DNA techniques and is known as recombinant human EPO (rhEPO). rhEPO has a molecular mass of approximately 36,000 Daltons, as determined by SDS-PAGE. The molecular mass of the protein backbone is 18,398 Daltons, which indicates that the entire molecule is heavily glycolsylated. The carbohydrate residues are important for in vivo biologic activity.

Maintaining proteins, such as rhEPO, in their native state in aqueous solution or in solid phase is a major challenge to those working in the field of pharmaceutical formulations. The existence of a protein in its native state depends on protein concentration, temperature and nature of solvent, ionic strength of the buffer, etc. Changes in any of these parameters can affect the stability of a protein in solution or solid phase.

Commercial preparations of rhEPO are presently sold as either dilute aqueous solutions or in a lyophilized form which is used to form a dilute aqueous solution, both of which are administered to the body by injection. The concentration of rhEPO in these preparations is very low and the rhEPO is cleared from the body fairly quickly after administration. In view of this limitation of present preparations, there is a need for concentrated preparations of rhEPO, e.g., those containing higher amounts of rhEPO, which can be used in alternate drug delivery systems. We used spray drying techniques to prepare such preparations.

The spray drying of pharmaceuticals is known in the art. For example, see Broadhead, J. et al., "The Spray Drying of Pharmaceuticals," in Drug Dev. Ind. Pharm, 18 (11 & 12), 1169–1206 (1992). In addition to small molecule pharmaceuticals, a variety of biological materials have been spray dried and these include: enzymes, sera, plasma, microorganisms and yeasts. Spray drying is a useful technique because it can convert a liquid pharmaceutical preparation into a fine, dustless or agglomerated powder in a one-step process. The basic technique comprises the following four steps:

a) atomization of the feed solution into a spray;

b) spray-air contact;

c) drying of the spray; and d) separation of the dried product from the drying air.

Although known in the field of pharmaceuticals, there has not been much use of spray drying for therapeutic proteins, such as rhEPO. One apparent reason for this is the concern that such proteins may be thermally degraded by the high temperatures utilized in the spray drying process. This is especially true of complex glycoproteins, such as rhEPO, which, in addition to their polypeptide backbones, also have complex branched carbohydrate portions that are required for biological activity. The availability of lyophilization as a ready alternative further steered workers in the field away from using spray drying for therapeutic proteins. However, spray drying provides certain advantages over lyophilization in that it is more economical, fast and easy to scale up. Also, spray dried powders are often more amenable to further processing than lyophilized powders.

It is usually impractical to design formulations based merely on the lyophilization of the bulk drug. This is so because many polypeptides are relatively unstable when lyophilized in low concentrations and they can adsorb to product packaging and lose activity. In order to overcome these problems, many lyophilized pharmaceutical compositions rely on the use of solid diluents, cryoprotectants or bulking agents to increase the amount of solid material present during the lyophilization process. As a result the final lyophilized material contains a small percentage (w/w) of active drug mixed with a large percentage of other solid material.

In contrast, the present invention provides a method for producing an rhEPO powder from bulk rhEPO wherein the powder produced is pure or essentially pure rhEPO or has a higher percentage (w/w) of rhEPO than can be prepared using traditional lyophilization techniques.

SUMMARY OF THE INVENTION

The present invention provides a method for preparing stable, spray dried rhEPO and the rhEPO powder produced thereby.

The method of the present invention comprises first providing an aqueous solution of rhEPO having a concentration within the range of about 20 mg/ml to about 100 mg/ml. That solution is then atomized into a spray and the spray is dried with hot air in order to evaporate the water from the spray. The dried rhEPO produced thereby is then separated from the drying air.

The initial aqueous solution may contain, in addition to rhEPO, excipients such as mannitol, glycine and/or a surfactant. The dry rhEPO composition produced by the method of the present invention comprises rhEPO in a concentration within the range of 4.0% to 100% (w/w) and has a residual moisture content within the range of about 3.0% to about 5.0% (w/w). The size of the particles of the composition are within the range of about 2.0 microns to about 6.0 microns.

DETAILED DESCRIPTION OF THE INVENTION

A concentrated rhEPO solution of at least 20 mg/ml was used for spray drying. The concentrated aqueous solution was atomized into fine droplets by pumping it through a nozzle with pressurized air. The droplets then entered a drying chamber and the water was evaporated by the hot drying air flowing co-current with the feed solution. As the water evaporated, solid rhEPO and excipients, if present, separated from the aqueous droplets. The dried rhEPO was carried by the drying air current to a cyclone separator for clarification, i.e., the dried rhEPO was separated from the drying air, and the dried product was collected in the collection vessel attached at the bottom of the cyclone separator. The drying air was then expelled through a fines scrubber into the atmosphere.

As used herein, the phrase "rhEPO" means any protein having all or part of the polypeptide backbone described for rhEPO in U.S. Pat. No. 4,703,008 and which possesses the biological property of causing bone marrow cells to increase production of reticulocytes and red blood cells and to increase hemoglobin synthesis or iron uptake. It is contemplated that biologically active fragments, analogs or chemically synthesized derivatives of EPO may be used in the present invention, rather than rhEPO, provided that such fragments or derivatives retain the biological activity of rhEPO. Certain EPO analogs are described in U.S. Pat. No. 4,703,008. Therefore, use of such biologically active EPO analogs, fragments, or derivatives is considered to be within the scope of the present invention.

The concentrated rhEPO powders produced by the present invention may be used in alternate drug delivery systems to deliver the rhEPO. One such system is a controlled release delivery system that delivers the rhEPO at a predetermined rate for a definite time period in the body. Alternatively, the concentrated rhEPO powders may be reconstituted with water for injection or normal saline to form aqueous solutions suitable for human therapeutic use. The controlled release systems mentioned above are envisioned to include rhEPO placed within a polymeric material, vesicles or a miniature pump, as well as macromolecular conjugates of rhEPO and other polymeric materials. These systems may then be used as subdermal reservoir implants of concentrated rhEPO. Non-limiting examples of these systems include matrices of solid hydrophobic polymers surrounding the rhEPO, such as non-degradable ethylene-vinylacetate copolymers or degradable lactic acid-glycolic acid copolymers. Such hydrophobic polymers may additionally take the form of microspheres.

The present invention provides stable rhEPO powder. As used herein, "stable" means that the rhEPO maintains its biological activity over time and its structure is maintained in its native state, i.e. it is not oxidized or otherwise degraded into another chemical species. Stability can be substantiated by RIA, Western Blot and in vivo or in vitro bioassays.

The following examples are presented to illustrate the subject invention. The invention is not to be considered limited by these examples, but only by the appended claims.

EXAMPLE 1

SPRAY DRYING PROCESS FOR rhEPO

This example describes a process of spray drying used to produce amorphous rhEPO exclusively in solid form or in conjunction with inert, pharmaceutically acceptable excipients. The so formulated amorphous bulk rhEPO is stable for at least 6 months at 5° C. storage (refrigerator). The current literature describing spray drying of therapeutic proteins is limited and does not discuss the stability of therapeutic proteins in the dried form at higher concentrations, such as 25% (w/w) and greater. For example, see Mumenthaler et al., Pharm. Res. 11:12–20 (1994). Furthermore, the current literature does not provide sufficient evidence of the stability of these proteins in the solid form. In fact, some of the literature shows unsatisfactory stability which may be attributed to the excipients or processing conditions that were used. For example certain inorganic salts, amino acids, surfactants etc. are known to stabilize proteins in solution. However, the presence of citrate salts in bulk rhEPO did not yield stable spray dried rhEPO. Therefore, bulk rhEPO was dialyzed into water for injection before spray drying. In order to obtain a satisfactory yield of the product upon spray drying, dialysis was continued until the concentration of the rhEPO was within the range 20–100 mg/mL. These concentrated bulk rhEPO solutions in water for injection showed satisfactory stability upon storage at 5° C. for at least 6 months. An alternative technique of preparing dry proteins, namely freeze drying, was not suitable for rhEPO because of its poor stability, irrespective of the presence of citrate salts (see Example 2).

The process for preparing solid rhEPO and rhEPO powder with excipients consisted of the following two steps:

A. Dialysis and concentration of bulk rhEPO; and

B. Spray drying of the dialyzed bulk rhEPO

A. Dialysis and Concentration

Bulk rhEPO supplied in 20 mM citrate buffer was dialyzed to remove all the citrate and replaced by water for injection. The dialysis was performed as follows:

Bulk rhEPO (200 mL) in citrate buffer (approx. conc. 2.0 mg/mL) was taken up in a Amicon® dialyzer fitted with a 10,000 molecular weight cut-off dialysis membrane. This dialysis cell was attached to a stainless steel vessel containing water for injection and the vessel was connected to a nitrogen gas tank. The dialysis was performed at 30–40 psi and continued until at least 2000 mL of dialysate was collected. The resulting aqueous solution of rhEPO devoid of any citrate was then concentrated to a final concentration of about 20 to about 100 mg/mL rhEPO. The resulting concentrated aqueous solution of rhEPO was then stored at 5° C. until it was spray dried. The concentrated rhEPO solutions were also monitored for rhEPO stability at 5° C.

B. Spray Drying

The spray drying process consisted of the following steps:
1. Atomization of the feed solution;
2. Spray-air contact;
3. Evaporation of the solvent;
4. Clarification of the dried solid from the drying gases. A laboratory scale spray dryer (Buchi®, Model 190) was used in the process.

1. Atomization:

Aqueous rhEPO solution was fed to the atomizer nozzle (0.5 mm I.D.) at room temperature using a peristaltic pump. The liquid feed was atomized into small droplets by high pressure air. Such atomization can also be achieved by using a rotating disc.

2. Spray-air contact and Evaporation:

As the droplets entered the evaporation chamber (105 mm I.D.×450 mm L), water was evaporated by the hot drying air flowing co-current. The temperature of the drying air varied from 64°–80° C. As the water evaporated, the solid separated from the aqueous solution in the shape of spheres or semi-spheres. The drying can also be performed by counter-current technique, where the drying air and the feed solution flow in the opposite direction.

3. Clarification:

The dried powder was carried by the drying air current to a cyclone separator for clarification. In the cyclone separator, the dried solid mass was separated from the drying air. The dried product was collected in a collection vessel attached at the bottom of the cyclone separator. The drying air (without the dried product) was expired through a fines scrubber into the atmosphere.

C. Chemical Characterization

A known amount of the spray dried rhEPO was dissolved in water for injection. This aqueous solution was then analyzed as follows:

1. Radio-immuno Assay (RIA):

The method used was that of Egrie et al., J Immunol Meth, 99: 235–241 (1987) This method consists of complexing rhEPO with rabbit polyclonal antibody (raised against rhEPO). This was achieved by incubating rhEPO with the rabbit polyclonal antibody overnight at refrigerated temperature. The incubation was continued for another additional day under the same conditions after adding $^{125}$I-EPO. The antigen-antibody complex was precipitated by goat anti-rabbit antibody, normal rabbit serum and polyethylene glycol. The precipitated complex was washed and the amount of bound $^{125}$I-EPO determined by using a gamma counter. This procedure was repeated for standard rhEPO solutions of known concentrations and test sample solutions. rhEPO concentrations of the test samples were calculated by comparing gamma counter readings with those of standard rhEPO solutions.

2. Western Blot:

The method used was that set forth in Egrie et al. Immunobiol, 172: 213–224 (1986). A 0.5 ug aliquot of denatured rhEPO was loaded on a standard (12.5%) sodium dodecyl sulphate-polyacrylamide gel (SDS-PAGE). Electrophoresis was performed and the gel was blotted onto a nitrocellulose membrane using a transfer buffer consisting of TRIS, glycine and methanol. This nitrocellulose membrane was blocked with 5% non-fat milk in TRIS buffered saline. The blocked nitrocellulose blot containing rhEPO was then conjugated with mouse-anti-human monoclonal antibody followed by goat anti-mouse polyclonal antibody. This complex was then stained using an alkaline phosphatase conjugate substrate kit. Each blot contained a standard rhEPO, standard rhEPO containing a known amount of rhEPO aggregates and test sample(s). The intensity of the rhEPO standard, and aggregate standard was compared with the test sample.

3. Mouse bioassay:

A known amount of spray dried rhEPO was reconstituted in water for injection. The biological activity of this solution was measured by monitoring the rate of incorporation of iron in exhypoxic mice after injecting the rhEPO solution. The method used was that of Cotes et al., Nature, 191:1065–1067 (1961).

TABLE 1

Formulation Examples:

| No. | Ingredients | Formulation # (quantities in gm.) | | | | |
|---|---|---|---|---|---|---|
| | | I | II | III | IV | V |
| 1. | rhEPO | 0.0813 | 0.162 | 1.5 | 25 | 25 |
| 2. | Glycine | 1.00 | 2.00 | 0 | 37.5 | 37.495 |
| 3. | Mannitol | 1.00 | 2.00 | 0 | 37.5 | 37.495 |
| 4. | Tween ™ 80 | 0.01 | 0 | 0 | 0 | 0.01 |
| 5. | WFI (q.s.) | 100 | 100 | 100 | 2000 | 2000 |

Note:
WFI = Water for Injection
Formulation No. II was spray dried at two different inlet temperatures of 64 and 80° C.

Five solutions were prepared by dissolving excipients such as mannitol, glycine and/or Tween® 80 in rhEPO concentrated aqueous solution one at a time with mild agitation. In the case of formulation III, no excipients were added. The formulations for these solutions are set forth above in Table 1. All of these solutions were spray dried according to the spray drying parameters listed as follows:

| | |
|---|---|
| Solution feed rate: | 1 mL/min |
| Air atomization rate: | 600–700 normliter/hr. |
| Drying air rate: | 32,000 to 45,000 liter/hr. |
| Inlet temperature: | 64–80° C. |
| Outlet temperature: | 46–65° C. |

After spray drying, the final solid rhEPO content for formulations I and II was approx. 4% (w/w), formulation III was 100% w/w and formulations IV and V were 25% (w/w) rhEPO. The residual moisture content varied from 3.0% to 5.0% (w/w) as determined by the Karl-Fisher method (USP XXIII-NF XVII, pp. 1840–1843, method 1a (1995)). The particle size was 4.1 microns ±1.89 for spray dried formulation III.

Preliminary experiments using bulk rhEPO containing citrate buffer did not yield stable spray dried rhEPO with mannitol, glycine and/or Tween® 80. Therefore, dialysis of the bulk rhEPO to remove citrate salts was essential for spray drying. In order to obtain a good yield upon spray drying, the feed solution had to have a solids content of at least 2%. Therefore, the dialyzed rhEPO solution was concentrated to 20–100 mg/mL.

It was determined that Tween® 80 was not necessary to produce stable spray dried rhEPO by comparing stability data on formulations I and II and formulations IV and V. Also, 6 month stability data on pure rhEPO suggests that mannitol and/or glycine may not be necessary for producing stable spray dried rhEPO. Thus, if used, mannitol and glycine merely seem to serve the function of bulking agents (as isotonic/isosmotic adjusting agents) that can be used to alter rhEPO concentration in the final spray dried rhEPO formulation.

The spray dried rhEPO of the present invention has advantages over lyophilized rhEPO. As a comparison, formulations I, II and III were also lyophilized (see Example 2). However, RIA data for the lyophilized samples stored for 2 months at 5° C. ranged from 73–78% of the label claim (LC). These low EPO potency values (as determined by RIA) at such a short storage duration indicate instability. Also, the 6 month lyophilized samples showed more than 2% EPO aggregates on SDS-PAGE after reconstitution. This indicates instability of the reconstituted rhEPO. Thus, spray dried formulations were more stable than freeze dried formulations of the same composition.

Stability tables of spray dried formulation numbers III and IV mentioned above are set forth below. In both cases, the samples were stored at 5° C. and the presence of rhEPO with less than 2% aggregates was confirmed at each measurement by Western blot analysis.

TABLE 2

Stability Data for Formulation #IV

| TIME | Expected Conc. (U/ml) | RIA *U/ml | RIA (% LC) |
|---|---|---|---|
| 0 | 31,500 | 35049 | 111 |
| 1 | 30,843 | 34188 | 111 |
| 2 | 30,121 | 29646 | 98 |
| 6 | 29,250 | 28521 | 97.5 |

TABLE 3

Stability Data for Formulation #III

| TIME | Expected Conc. (U/mL) | RIA (U/ml) | RIA (% LC) |
|---|---|---|---|
| 0 | 142,169 | 120339 | 84 |
| 1 | 123,614 | 96295 | 78 |
| 2 | 120,482 | 106523 | 88 |
| 3 | 125,542 | 109520 | 87 |
| 6 | 118,554 | 115441 | 97 |

EXAMPLE 2

LOPHILIZATION PROCESS FOR EPO

The example describes a process of lyophilization used to produce dried rhEPO in pure form or with a combination of pharmaceutically acceptable excipients. The stability of the rhEPO which was lyophilized was determined and the results are presented below. All of the rhEPO preparations used in this example were also spray dried as described above. The RIA and Western Blot procedures were performed essentially as described above for the spray dried rhEPO example.

A typical lyophilization cycle for freeze drying rhEPO solutions without excipients began by freezing the solution to about −40° C. and holding at the temperature for about three hours to ensure that the solution was completely frozen. As the solution was being frozen the condenser temperature was lowered to about −50° C. The primary drying was carried out by first lowering the pressure in the drying chamber to about 200 millitorr, and the system was allowed to stabilize for about three hours. The temperature was then raised to about −30° C. at the rate of about 0.1° C. per minute. The drying (by subliming ice to water vapor) was continued for about 60 hours. Secondary drying was performed by raising the temperature of the product to about 15° C. at the rate of about 0.5° C. per minute. The pressure in the drying chamber was further reduced from about 200 millitorr to about 100 millitorr. The secondary drying phase was continued for about 16 hours to ensure complete drying. Following the secondary drying, the vials were capped and sealed. The sealed vials were stored at about 5° C. until being removed for stability testing described below. For stability testing, the contents of the vial was reconstituted with water, and analyzed by RIA and Western Blot. The results of the stability testing were compiled as a percentage of rhEPO remaining. Lower percentages of rhEPO remaining demonstrate poor stability. Western Blot results determine whether the rhEPO is in a native form or in a denatured, aggregated form. Samples of rhEPO which have greater than 2% aggregates, as compared to a 2% aggregated rhEPO standard, are determined to have poor stability. The results of the stability tests performed on lyophilized rhEPO in different formulations is presented in Table 4.

TABLE 4

Stability as Percent Label Claim of EPO in Freeze Dried Formulation at 5° C.

| | RIA | | | Western Blot | | | |
|---|---|---|---|---|---|---|---|
| Formulation | Initial | 1 mo. | 2 mos. | Initial | 1 mo. | 2 mo. | 6 mos. |
| I | 93.2 | 71.5 | 75.0 | Presence of EPO confirmed | | | more than 2% |
| II | 82.0 | 76.5 | 72.9 | | | | |
| III | 79.6 | 69.7 | 78.1 | Less than 2% Aggregate | | | Aggregate |

The data shown in Table 4 demonstrated that lyophilized rhEPO does not remain as stable as spray dried rhEPO. Therefore, spray drying of rhEPO produces a more stable product compared with lyophilization. The present invention therefore provides stable spray dried rhEPO which can be prepared without the addition of any excipients or stabilizers, such as cyclodextrins, glycine, mannitol or Tween 80. An excipient-free preparation of rhEPO is desirable for certain drug delivery systems, such as delivery by pulmonary route, that usually require the drug to be as free from excipients as possible.

The invention has been described herein with reference to certain preferred embodiments and examples. Since obvious variations will appear to those skilled in the art, the invention is not to be considered limited thereto, but only by the claims which follow.

What is claimed is:

1. A method for preparing spray dried recombinant human erythropoietin (rhEPO), comprising:
    a) providing an aqueous solution of rhEPO having a concentration within the range of about 20 mg/ml to about 100 mg/ml;
    b) atomizing said solution into a spray;
    c) drying said spray with hot drying air in order to evaporate the water from the spray to form a dried rhEPO; and
    d) separating dried rhEPO from the drying air to provide biologically active spray dried rhEPO.

2. The method of claim 1, wherein the aqueous solution of rhEPO contains no salts or other additives.

3. The method of claim 1, wherein the aqueous solution is dialyzed to remove salts prior to step (b).

4. The method of claim 1, wherein the solution is atomized by feeding it into a nozzle under pressure.

5. The method of claim 1, wherein the spray and drying air are passed through the dryer in the same direction.

6. The method of claim 1, wherein the dried rhEPO is separated in a cyclone separator.

7. The method of claim 1, wherein the drying is conducted within a temperature range of about 60° C. to about 85° C.

8. Dry rhEPO produced by the method of claim 1 that is substantially free from urea and added stabilizers.

9. The rhEPO of claim 8 which is 100% EPO (w/w).

* * * * *